(12) United States Patent
James et al.

(10) Patent No.: US 9,427,329 B2
(45) Date of Patent: Aug. 30, 2016

(54) SPINAL IMPLANTS

(71) Applicant: Meditech Spine, LLC, Atlanta, GA (US)

(72) Inventors: Stephen B. James, Cumming, GA (US); Adam Sclafani, Uniontown, OH (US); Eric Flickinger, Atlanta, GA (US)

(73) Assignee: MEDITECH SPINE, LLC, Atlanta, GA (US)

( * ) Notice: Subject to any disclaimer, the term of this patent is extended or adjusted under 35 U.S.C. 154(b) by 0 days.

(21) Appl. No.: 14/528,843

(22) Filed: Oct. 30, 2014

(65) Prior Publication Data

US 2015/0051705 A1    Feb. 19, 2015

Related U.S. Application Data

(63) Continuation of application No. 13/222,729, filed on Aug. 31, 2011, now Pat. No. 8,900,309.

(60) Provisional application No. 61/378,445, filed on Aug. 31, 2010.

(51) Int. Cl.
*A61F 2/44* (2006.01)
*A61F 2/28* (2006.01)
*A61F 2/30* (2006.01)

(52) U.S. Cl.
CPC ............ *A61F 2/4465* (2013.01); *A61F 2/442* (2013.01); *A61F 2/447* (2013.01); *A61F 2002/2835* (2013.01); *A61F 2002/3023* (2013.01); *A61F 2002/3083* (2013.01); *A61F 2002/30266* (2013.01); *A61F 2002/30822* (2013.01); *A61F 2002/30828* (2013.01); *A61F 2002/30904* (2013.01); *A61F 2002/4475* (2013.01)

(58) Field of Classification Search
CPC ............... A61F 2/44; A61F 2/442; A61F 2/4455–2/447; A61F 2002/4475; A61F 2002/30822; A61F 2002/30878–2002/30904; A61F 2002/30841–2002/30848
See application file for complete search history.

(56) References Cited

U.S. PATENT DOCUMENTS

| | | | |
|---|---|---|---|
| 4,834,757 | A | 5/1989 | Brantigan |
| 5,306,308 | A | 4/1994 | Gross et al. |
| 5,702,449 | A | 12/1997 | McKay |
| 5,865,848 | A | 2/1999 | Baker |
| 5,888,222 | A | 3/1999 | Coates et al. |
| 5,989,289 | A | 11/1999 | Coates et al. |
| 6,143,033 | A | 11/2000 | Paul et al. |
| 6,290,724 | B1 | 9/2001 | Marino |
| 6,325,827 | B1 | 12/2001 | Lin |
| 6,346,122 | B1 | 2/2002 | Picha et al. |

(Continued)

OTHER PUBLICATIONS

Atomic®, "*Cervical Plate System*", Illustration, available at least as early as Aug. 30, 2009, 1 page.

(Continued)

*Primary Examiner* — Jacqueline Johanas
(74) *Attorney, Agent, or Firm* — Kilpatrick Townsend & Stockton LLP

(57) ABSTRACT

Disclosed are improved spinal implants that are configured to help prevent post-operative migration of the implant. In some embodiments, the implant system includes multi-axial tooth geometry and other geometrical configurations such as but not limited to peripheral curvatures that aid in the prevention of such post-operative migration. Also disclosed are asymmetrical implants having superior and inferior surfaces with different angulations relative to the sagittal midline.

15 Claims, 10 Drawing Sheets

(56) References Cited

U.S. PATENT DOCUMENTS

| | | | |
|---|---|---|---|
| 6,416,551 B1* | 7/2002 | Keller | A61F 2/4425 623/17.11 |
| 6,458,159 B1 | 10/2002 | Thalgott | |
| 6,468,311 B2 | 10/2002 | Boyd et al. | |
| 6,478,800 B1 | 11/2002 | Fraser et al. | |
| 6,520,993 B2 | 2/2003 | James et al. | |
| 6,592,624 B1 | 7/2003 | Fraser et al. | |
| 6,623,525 B2 | 9/2003 | Ralph et al. | |
| 6,716,245 B2 | 4/2004 | Pasquet et al. | |
| 6,827,740 B1 | 12/2004 | Michelson | |
| 7,077,864 B2 | 7/2006 | Byrd, III et al. | |
| 7,166,129 B2* | 1/2007 | Michelson | A61F 2/4455 623/17.11 |
| 7,172,627 B2 | 2/2007 | Fiere et al. | |
| 7,238,203 B2 | 7/2007 | Bagga et al. | |
| 7,244,275 B2* | 7/2007 | Michelson | A61F 2/4455 623/16.11 |
| 7,615,077 B2 | 11/2009 | Melkent et al. | |
| 7,727,279 B2 | 6/2010 | Zipnick et al. | |
| 7,806,932 B2 | 10/2010 | Webb et al. | |
| 7,837,732 B2 | 11/2010 | Zucherman et al. | |
| 7,850,736 B2 | 12/2010 | Heinz | |
| 7,875,080 B2 | 1/2011 | Puno et al. | |
| 7,883,542 B2 | 2/2011 | Zipnick | |
| 7,918,888 B2 | 4/2011 | Hamada | |
| 8,043,377 B2 | 10/2011 | Guyer et al. | |
| 8,241,359 B2 | 8/2012 | Davis et al. | |
| 8,349,015 B2 | 1/2013 | Bae et al. | |
| 8,394,125 B2 | 3/2013 | Assell et al. | |
| 8,603,175 B2 | 12/2013 | Thibodeau | |
| 8,900,309 B2 | 12/2014 | James et al. | |
| 2001/0056302 A1 | 12/2001 | Boyer, II et al. | |
| 2002/0087212 A1 | 7/2002 | James et al. | |
| 2003/0181981 A1 | 9/2003 | Lemaire | |
| 2004/0127990 A1 | 7/2004 | Bartish, Jr. et al. | |
| 2005/0125062 A1 | 6/2005 | Biedermann et al. | |
| 2005/0143822 A1 | 6/2005 | Paul | |
| 2006/0129241 A1 | 6/2006 | Boyer et al. | |
| 2006/0136059 A1* | 6/2006 | Thramann | A61F 2/44 623/17.11 |
| 2006/0167548 A1 | 7/2006 | Jackson | |
| 2006/0235535 A1* | 10/2006 | Ferree | A61F 2/28 623/17.16 |
| 2006/0241760 A1 | 10/2006 | Randall et al. | |
| 2006/0247775 A1* | 11/2006 | Thramann | A61F 2/44 623/17.11 |
| 2007/0055374 A1 | 3/2007 | Copf, Jr. et al. | |
| 2007/0100455 A1* | 5/2007 | Parsons | A61F 2/4425 623/17.14 |
| 2007/0162138 A1 | 7/2007 | Heinz | |
| 2007/0198089 A1* | 8/2007 | Moskowitz | A61F 2/442 623/17.11 |
| 2007/0233263 A1* | 10/2007 | Melkent | A61F 2/30771 623/17.16 |
| 2007/0255414 A1* | 11/2007 | Melkent | A61F 2/4465 623/17.16 |
| 2007/0270951 A1 | 11/2007 | Davis et al. | |
| 2007/0270963 A1 | 11/2007 | Melkent et al. | |
| 2008/0015698 A1* | 1/2008 | Marino | A61F 2/4425 623/17.15 |
| 2008/0051890 A1 | 2/2008 | Waugh et al. | |
| 2008/0051901 A1 | 2/2008 | de Villiers et al. | |
| 2008/0065222 A1* | 3/2008 | Hamada | A61F 2/4465 623/17.16 |
| 2008/0071372 A1 | 3/2008 | Butler et al. | |
| 2008/0097610 A1* | 4/2008 | Guyer | A61F 2/30771 623/17.16 |
| 2008/0103602 A1 | 5/2008 | Berry et al. | |
| 2008/0161927 A1* | 7/2008 | Savage | A61F 2/4455 623/17.16 |
| 2008/0275506 A1* | 11/2008 | Baynham | A61F 2/447 606/261 |
| 2009/0076613 A1* | 3/2009 | Biedermann | A61F 2/442 623/17.16 |
| 2009/0099601 A1 | 4/2009 | Aferzon et al. | |
| 2009/0216330 A1 | 8/2009 | Geisert et al. | |
| 2009/0222092 A1 | 9/2009 | Davis et al. | |
| 2009/0234458 A1 | 9/2009 | de Villiers et al. | |
| 2010/0004752 A1 | 1/2010 | White et al. | |
| 2010/0070039 A1* | 3/2010 | Guyer | A61F 2/447 623/17.16 |
| 2010/0125334 A1 | 5/2010 | Krueger | |
| 2010/0137674 A1* | 6/2010 | Evans | A61N 5/1027 600/7 |
| 2010/0152853 A1 | 6/2010 | Kirschman | |
| 2010/0191337 A1 | 7/2010 | Zamani et al. | |
| 2010/0228296 A1 | 9/2010 | Vraney et al. | |
| 2010/0268339 A1 | 10/2010 | Malinin et al. | |
| 2010/0286777 A1 | 11/2010 | Errico et al. | |
| 2010/0305706 A1 | 12/2010 | Webb et al. | |
| 2011/0022089 A1* | 1/2011 | Assell | A61F 2/4405 606/247 |
| 2011/0040382 A1 | 2/2011 | Muhanna | |
| 2011/0184523 A1* | 7/2011 | Blackwell | A61F 2/4455 623/17.16 |
| 2011/0251691 A1* | 10/2011 | McLaughlin | A61F 2/44 623/17.16 |
| 2011/0264218 A1 | 10/2011 | Asaad | |
| 2012/0109315 A1 | 5/2012 | Lechmann et al. | |
| 2012/0215315 A1 | 8/2012 | Hochschuler et al. | |
| 2012/0290091 A1 | 11/2012 | Kirschman | |
| 2012/0310356 A1 | 12/2012 | Davis et al. | |

OTHER PUBLICATIONS

Biomet, Inc., "ESL", EBI LLC., USA, 2009, 15 pages.

Biomet, Inc., "Solitaire Anterior Spinal System, Independent Stabilization for The Anterior Column", EBI LLC., USA, 2009, 19 pages.

Crystal® "Cervical Interbody System", Illustration, available at least as early as Aug. 30, 2009, 1 page.

Depuy, "Bengal® Stackable Cage System", Illustration, available at least as early as Aug. 30, 2009, 1 page.

Depuy, "Bengal® System", Illustration, available at least as early as Aug. 30, 2009, 1 page.

Globus Medical, "Colonial®", Illustration, available at least as early as Aug. 30, 2009, 1 page.

K2M, Illustration, available at least as early as Aug. 30, 2009, 1 page.

Lucent Magnum®, "ALIF Interbody System", Illustration, available at least as early as Aug. 30, 2009, 1 page.

Lucent®, "PLIF Interbody System", Illustration, available at least as early as Aug. 30, 2009, 1 page.

Lucent®, "TLIF Interbody System", Illustration, available at least as early as Aug. 30, 2009, 1 page.

Magnum™, "Stand-Alone, No Profile ALIF", Illustration, available at least as early as Aug. 30, 2009, 1 page.

Medtronic, "Verte-Stack Boomerang, Peek Vertebral Body Spacer", ©Medtronic Sofamor Danek, USA, Inc., 2006, 6 paqes.

Medtronic, Cornerstone PEEK Cage, Biomet Spine, "C-Thru™, Anterior Spinal System", Brochure, available at least as early as Aug. 30, 2009, 4 pages.

Mercury® Classic, "Pedicle Screw System", Illustration, available at least as early as Aug. 30, 2009, 1 page.

Mosaic®, "Cervical Implant System", Illustration, available at least as early as Aug. 30, 2009, 1 page.

Orthofix, "Construx Mini PEEK Partial VBR System", Illustration, available at least as early as Aug. 30, 2009, 1 page.

Pioneer Surgical, C-Plus™, PEEK-OPTIMA is a registered trademark of Invibio, Illustration, available at least as early as Aug. 30, 2009, 1 page.

Rabea Signus, Illustration, available at least as early as Aug. 30, 2009, 1 page.

Spinal Elements, "Delivering A New Standard", Illustration, available at least as early as Aug. 30, 2009, 1 page.

Synthes, "Cervios ChronOS", Illustration, available at least as early as Aug. 30, 2009, 1 page.

Notice of Allowance for U.S. Appl. No. 13/222,729 mailed on Jul. 30, 2014, 11 pages.

(56) References Cited

OTHER PUBLICATIONS

Final Office Action for U.S. Appl. No. 13/222,729 mailed on May 14, 2014, 22 pages.
Non-Final Office Action for U.S. Appl. No. 13/222,729 mailed on Sep. 25, 2013, 30 pages.
Final Office Action for U.S. Appl. No. 13/222,729 mailed on May 30, 2013, 26 pages.
Non-Final Office Action for U.S. Appl. No. 13/222,729 mailed on Jan. 17, 2013, 21 pages.

* cited by examiner

SPINAL IMPLANTS

RELATED APPLICATIONS

The present application is a Continuation of U.S. Ser. No. 13/222,729 filed Aug. 31, 2011 (Allowed); which application claims the benefit of U.S. Provisional Appln. No. 61/378,445 filed Aug. 31, 2010; the entire contents which are incorporated herein by reference in their entirety for all purposes.

FIELD OF THE INVENTION

This invention generally relates to surgical implants for use in spinal surgery.

BACKGROUND

Degenerative disc disease is typically caused by a loss of disc space height, leading to a narrowing of the neural foramen and subsequent neural compression, and causing back and radicular pain. Instability of the posterior elements can lead to conditions such as spondylolisthesis or spinal stenosis. In the case of spondylolisthesis, a vertebral body slips forward in relation to an adjacent vertebrae. This movement of the vertebral body narrows the foramen and results in painful pressure on the nerve roots. In the case of spinal stenosis, the spinal canal narrows and compresses the spinal cord and nerves.

Degenerative disc disease may often be resolved through a spinal fusion procedure using an interbody implant (one which is implanted between the bodies of two adjacent vertebrae). Interbody implants have been used since the mid 1930s to aid in spinal fusion. Such interbody implants may be formed from titanium, carbon fiber, allograft, or other suitable material including, but not limited to, biocompatible materials such as the Paek family of polymers. Implantation of a substitute graft is designed to reestablish normal disc height, provide immediate stability to the motion segment, and provide a matrix for fusion of the implant with the patient's natural bone structures. Bone tissue is capable of regeneration and will grow if adequate space is provided. Therefore, when the patient's bone grows into the implant device, the fusion becomes solid and movement is eliminated at that level. Additionally, non fusion techniques have been introduced to aid in motion preservation of the disc space. These are known as total disc replacements (TDR). A mechanical device is implanted into the disc space much like a fusion device but its goal is to prevent fusion of the interbody space and preserve movement in the motion segment. These devices are made from various materials similar to fusion devices. Also, nucleus replacement devices have been introduced to preserve the annulus and maintain disc height. These devices are small and can be introduced to the disc space like fusion devices but through smaller incisions.

Typically, an open implant device is filled with a graft material and placed inside the disc space. Such graft material may come from the patient's own body. Alternatively, the graft material may be any suitable artificial, synthetic, or natural substitute. Once the implant containing the graft material is properly placed in the disc space, a biological reaction is triggered, which results in bone growth. Over time, as the patient's native bone begins to grow, the natural bone replaces the graft material, resulting in new bone located in the target region of the spine.

In order for the patient's native bone to grow appropriately, it is important that the implant remain properly in place in the interbody space. Typical implants employ many different approaches to implant contours in an effort to minimize post-operative migration of the implant. These approaches typically provide a tooth geometry and alignment designed to resist movement and migration along the anterior-posterior axis. This single axis implant geometry combined with the unnatural, non-anatomical implant shape typically also results in contact between the implant and vertebral endplates at discreet points. These point contacts may result in substantial discomfort and pain for the patient and contribute very little to the prevention of post-operative migration of the implant. In fact, the non-optimal contact between the implant and the vertebral walls increases the likelihood of post-operative movement of the implant, decreases the chance for fusion, and increases Pseudoarthrodesis.

The interbody space for lumbar surgery has always challenged surgeons trying to access the space to achieve arthrodesis. Multiple surgical methods have been employed to place the interbody implant into the disc space: a posterior approach (posterior lumber interbody fusion—PLIF), a transforaminal approach (transforaminal lumbar interbody fusion—TLIF), an anterior approach (anterior lumbar interbody fusion—ALIF) or a direct lateral approach (extreme lateral interbody fusion—XLIF).

Proper distraction during a PLIF procedure must be achieved to gain compression of the implant through ligamentous taxis. Proper distraction allows natural compression across the disc space via the annulus and other posterior elements as well as the anterior longitudinal ligament. This compression delivered to the implant helps stabilize the implant, which prevents expulsion, and keeps the grafting material under stress, thus promoting faster fusion and bone healing. Existing techniques for reaching the interbody space from a posterior approach include the use of Cloward dowels, threaded cages, impacted cages and impacted allografts. All of these techniques have limitations as well as complications, as they involve extensive nerve root retraction as well as destabilization through destruction of bony and ligamentous structures.

TLIF involves the removal of one facet joint, usually on the more diseased or symptomatic side of the spine. PLIF is usually performed bilaterally, removing a portion (if not all) of each of the facet joints. Removal of the entire facet joint improves visualization into the disc space, allowing removal of more disc material and insertion of a larger implant. The transforaminal approach limits the nerve root injuries associated with the PLIF procedure because the disc space and spinal canal is approached from one side of the intervertebral space. This allows the surgeon to operate with minimal stretching of nerve roots. Various banana-shaped implants have been designed to be impacted across the disc space to achieve arthrodesis. Although longer, straight implants have been placed across the disc space with some success, the lordotic angle of the spine is harder to properly match with these straight implants. The banana-shaped implant helps maintain proper lordosis when it is placed in the anterior third of the disc space. Despite the benefits of the TLIF procedure, TLIF still suffers from limitations involving bony and soft tissue destruction and bilateral pathology.

ALIF is utilized to avoid the posterior structures of the spine. However, the anterior approach (from the patient's abdomen) to the disc space also presents challenges and limitations because of the potential of vascular injuries. In addition, not all of the lumbar spinal segments can be reached from an anterior incision without potential complications. Retroperitoneal approaches have helped eliminate some of the vascular injuries, but the potential still exists. It is known in the art that revision surgery is greatly complicated by scarring from the initial procedure.

XLIF was devised in an attempt to avoid the complications associated with the posterior and anterior approaches to the spine. This technique provides an additional way to access the interbody space for fusion as well as for motion preservation procedures. XLIF is useful for lumbar fusions from L1-L5 and preserves the entire posterior envelope of the spine. The XLIF procedure can also be performed at levels above the lumbar spine in the thoracic region. XLIF is minimally invasive in that it does not involve cutting muscle tissue. While there is potential for nerve injury (though limited by using nerve monitoring equipment) and psoas muscle irritation, the muscles are spared through dilation instruments. Once the disc space is exposed, complete discectomy can be performed to prepare the fusion bed. Since the XLIF procedure avoids anterior entry, vascular structures are not compromised or scarred, eliminating possible complications in following salvage procedures. Another drawback of existing systems and techniques for XLIF procedures is that implants are usually undersized from a medial-lateral and anterior-posterior approach. When the implant is undersized, and not resting on the cortical edges of the vertebral bodies, they can piston through or subside into the softer, interior portions of the vertebral bodies. This can occur with or without endplate sparing techniques.

Each approach has its limitations as well as advantages. From a posterior (PLIF) or transforaminal (TLIF) approach, the individual implants are usually smaller because of the neural structures that prevent access to the total disc space. From an anterior (ALIF) or far lateral (XLIF) approach, the implants are usually quite larger and a fuller, more complete discectomy can be performed without the limitations of retracting neural structures. Thus, larger implants can be utilized that hold more graft material. Regardless of the approach, each implant inserted into the disc space will hold a volume of graft material with the intent of triggering the bone growth biological response.

Although the ALIF, PLIF, TLIF and XLIF approaches are discussed above, other approaches have also been developed. These and future approaches may be implemented in connection with the present invention. In addition to the fusion devices described herein, the same concepts of tooth geometry and implant angles (both symmetrical and asymmetrical) can be applied to non-fusion devices. Non fusion devices may include total disc replacement implants implanted singly or in pairs from anterior, lateral, transforaminal, posterior, anteriolateral, laparasccopic or any comparable approach. The design is also applicable to nucleus replacement devices for the disc space.

In existing systems, regardless of the surgical approach, the implants are not designed to fit the anatomical contours of the spinal cavity. Thus, the implants are subject to post-operative migration and repulsions, resulting in significant pain and discomfort for the patient. What is needed is a spinal implant designed to fit the anatomical contours of the spinal cavity that prevents movement and migration of the implant.

BRIEF SUMMARY

The terms "invention," "the invention," "this invention" and "the present invention" used in this patent are intended to refer broadly to all of the subject matter of this patent and the patent claims below. Statements containing these terms should be understood to not limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to the appropriate portions of the entire specification of this patent, any or all drawings and each claim.

Disclosed are improved surgical implant systems configured to maximize stability of the implant under various anatomical conditions. In some embodiments, the implant has a multi-axial tooth geometry that helps prevent post-operative migration of the implant and/or that helps improve the stability of the surgical implant. Additionally or alternatively, the implant has surface contours that help eliminate points of contact between the implant and the endplate and thus help improve stability of the implant.

Also additionally or alternatively, the implant may be asymmetrical. Specifically, in some embodiments, the implant has inferior and superior surfaces with angulations that are asymmetric relative to the implant midplane. Additionally or alternatively, the curvature of the inferior and superior surfaces may be asymmetric in either or both the medial-lateral plane or the anterior-posterior plane.

The above features, which may be used in conjunction with one another or separately, help align the implant more closely to the intervertebral space and/or resist motion along both axes of the endplate planes by improved contact of the implant with the endplate surfaces. Such improved contact enhances the performance and stability of these surgical implants.

DETAILED DESCRIPTION OF EMBODIMENTS OF THE INVENTION

Disclosed are interbody implant systems comprising implants with unique profiles and/or other features that help prevent movement and migration of the implants once the implants have been placed in the interbody disc space. The interbody implants are useful for implants of any size or style, but are particularly useful for implants of larger size that may be used in procedures such as ALIF or XLIF. The disclosed implants may also be used in other procedures, such as TLIF and PLIF. The interbody implants may be made of titanium, carbon fiber, allograft, or other suitable material including, but not limited to, biocompatible materials such as the Paek family of polymers. Those of ordinary skill in the art will readily appreciate other materials of which the implants may be composed.

As described in detail below, features of the disclosed implants maximize stability of the implant under various anatomical conditions. In some embodiments, the implant includes surface contours that better match the contours of the endplates, as described in detail below. Additionally or alternatively, the implant may include a plurality of tooth edges that are arranged to help resist migration of the implant in two directions. Additionally or alternatively, the implant may be asymmetric, as described in detail below.

Figure 1:
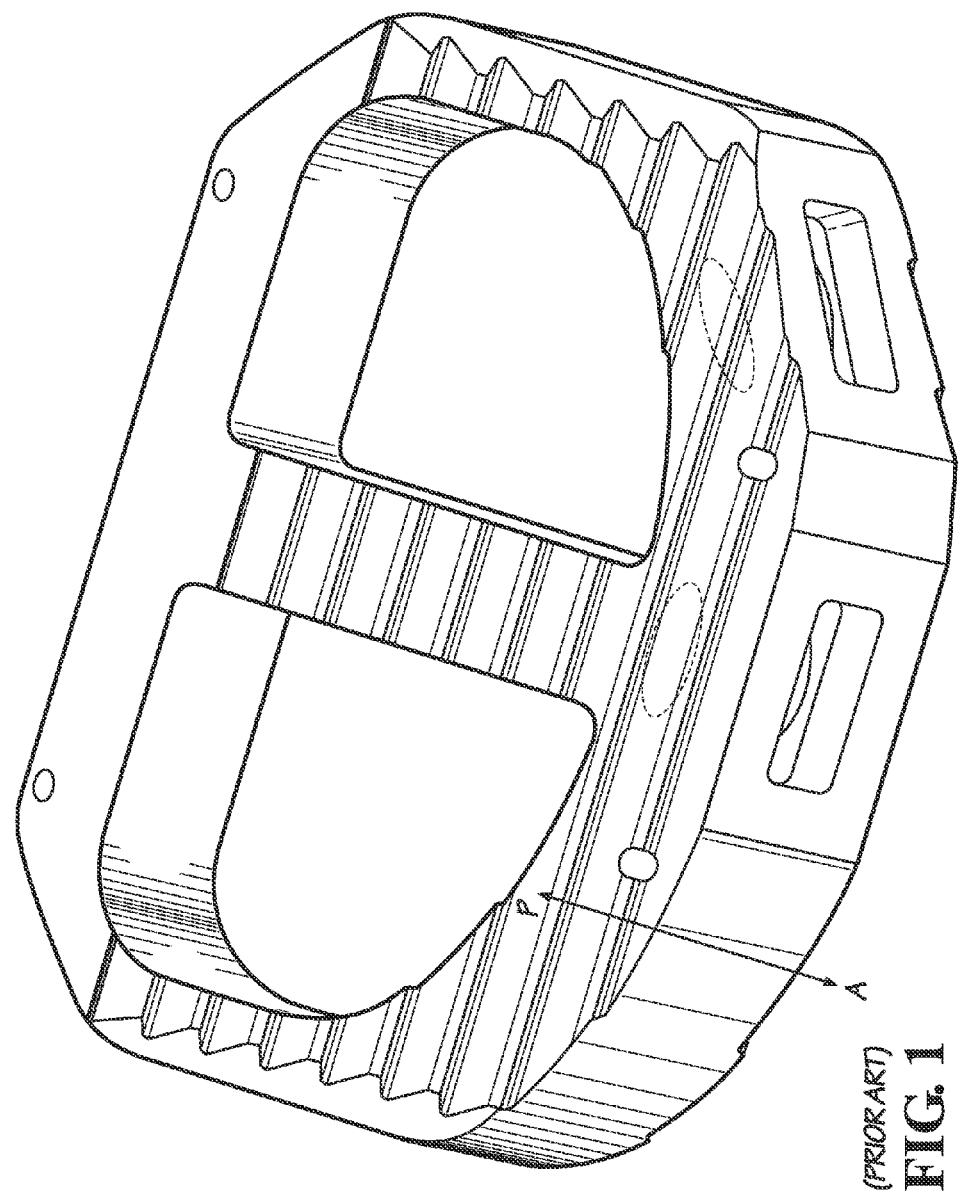
FIG. 1 is a perspective view of a prior art implant with single axis tooth geometry.

Typical implants employ the use of a tooth geometry to reduce post operative migration of the implant. However, as can be seen in FIG. 1, the tooth geometry of typical implants is aligned along a single anterior-posterior axis, resulting in the resistance of migration only in that one direction. While this design may reduce migration along the anterior-posterior axis, the design of prior implants does very little to prevent migration in other directions, such as the superior-inferior or medio-lateral axes.

Figure 2:
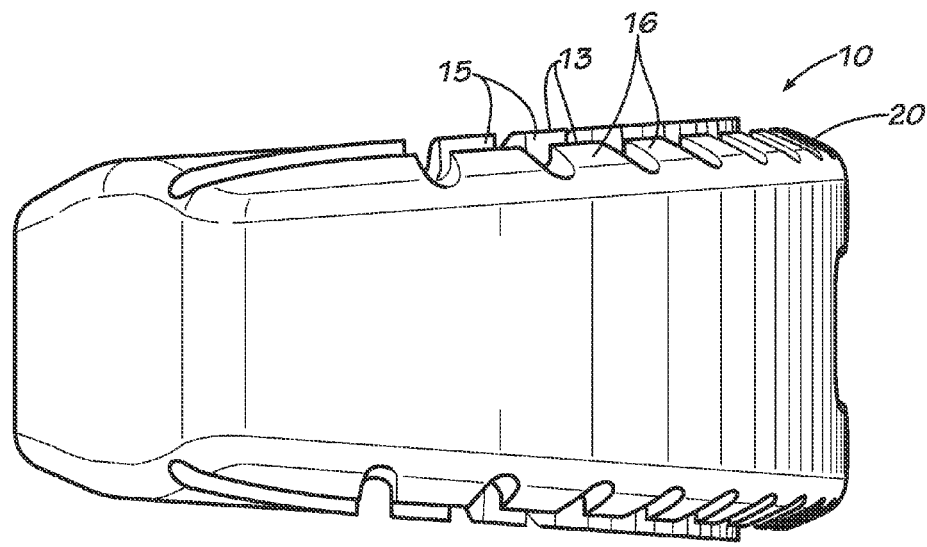
FIG. 2 is a lateral view of a symmetrical implant with radial tooth geometry according to one embodiment.
Figure 3:
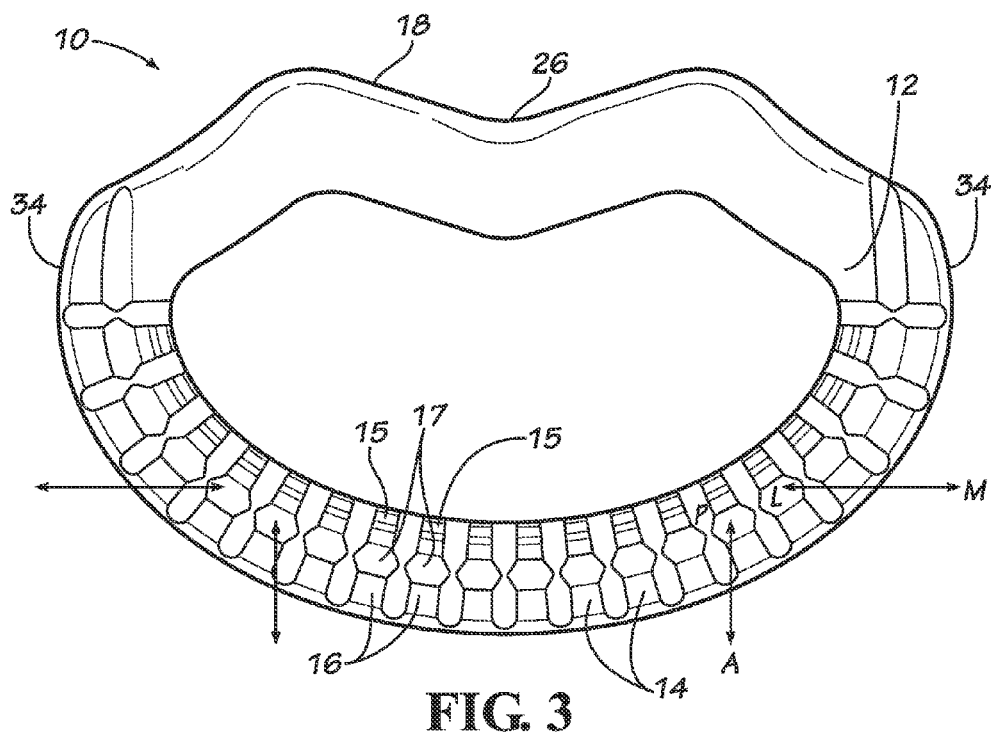
FIG. 3 is a top plan view of the implant of FIG. 2.
Figure 4:
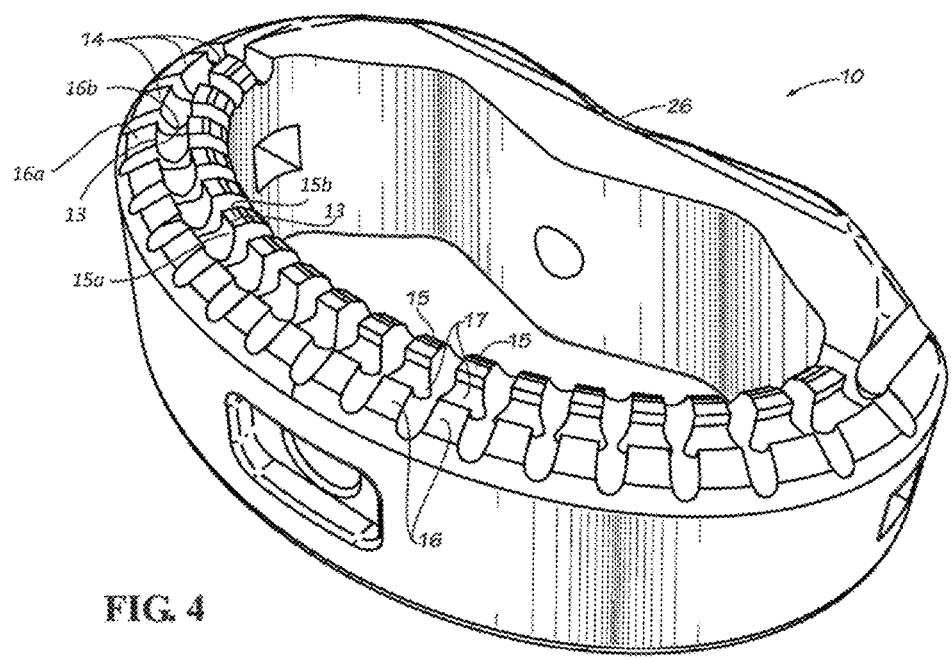
FIG. 4 is a perspective view of the implant of FIG. 2.

In certain embodiments, the implants comprise at least one exterior surface with a multi-axial tooth geometry pattern. For example, as shown in FIGS. 2-4, implant 10, which is generally kidney-bean shaped, comprises an exterior surface 12 with teeth 14 arranged in a circumferential or radial pattern. Teeth 14 may include a row of inner teeth 15 and a row of outer teeth 16, with an optional trough 17 separating the inner row of teeth 15 from the outer row of teeth 16. In some embodiments, as shown in FIG. 2, the inner teeth 15 are taller than the outer teeth 16 to help prevent translation or migration of the implant by better fitting to the concavity of the disc space. Teeth 14, including outer teeth 16 and inner teeth 15, each include an edge 13 at a peak of each tooth (FIGS. 2 and 4, edges 13 are formed by outer side 16a and inner side 16b of outer teeth 16 and by outer side 15a and inner side 15b of inner teeth 15) configured to contact with the endplate. The edges 13 are configured to provide bi-axial restriction of movement or migration of the implant. Specifically, as shown in FIGS. 3-4, the circumferential alignment of the teeth (and thus the edges 13 being non-parallel to one another) impedes movement and migration of the implant along at least two axes, the medial-lateral (M-L) axis and the anterior-posterior (A-P) axis. As shown in FIG. 4, inner teeth 15 taper inwardly such that a slope of the outer side 15a from the respective tooth edge 13 toward the sagittal midline is greater than a slope of the inner side 15b of each respective inner tooth 15 from the respective tooth edge 13 toward the sagittal midline. As shown in FIG. 4, outer teeth 16 taper outwardly or opposite from an inwardly adjacent inner tooth 15 such that a slope of the outer side 16a from the respective tooth edge 13 toward the sagittal midline is less than a slope of the inner side 16b of each respective outer tooth 16 from the respective tooth edge 13 toward the sagittal midline. Further, as shown in FIG. 4, the outer teeth 16 have an outer side 16a with a slope from the edge 13 toward the sagittal midline that is greater than a slope of the inner side 15b of the inner teeth 15 from the respective tooth edge 13 toward the sagittal midline. The pattern of the teeth may be linear, radial, chevron (shown below), or any other suitable arrangement. Moreover, the cross sectional geometry of the teeth 14 and the teeth edges 13 may also vary so long as the edges 13 have sufficient surface area to help reduce migration of the implant. In some embodiments, teeth 14 have a generally sawtooth shape, although the teeth 14 may have other profiles in different embodiments.

As shown in FIG. 2, teeth 14 may be arranged along both the superior and inferior surface of the implant, or may be arranged along only one of such surfaces in other embodiments. In some embodiments, the peripheral geometry of the implant, such as arcuate sides 34 (FIG. 3) and/or curvature 20 (FIG. 2 and described below), helps provide a more anatomical fit into the disc space, providing additional resistance to migration through better contact with the endplate surfaces.

Figure 5:
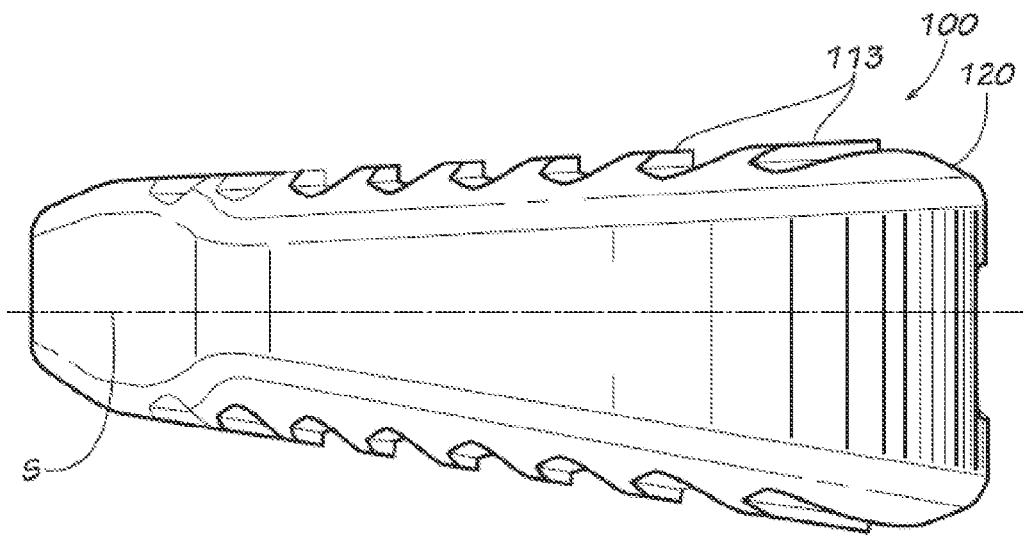
FIG. 5 is a lateral view of an asymmetrical implant according to another embodiment.
Figure 6:
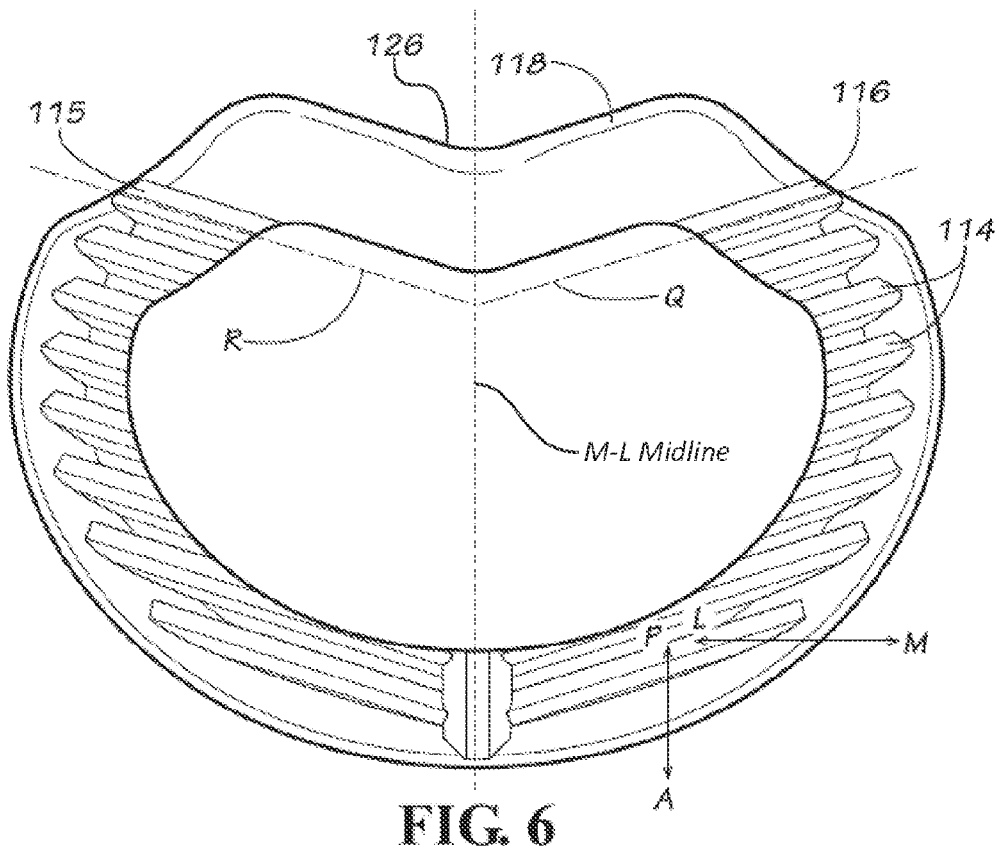
FIG. 6 is a top plan view of the implant of FIG. 5.
Figure 7:
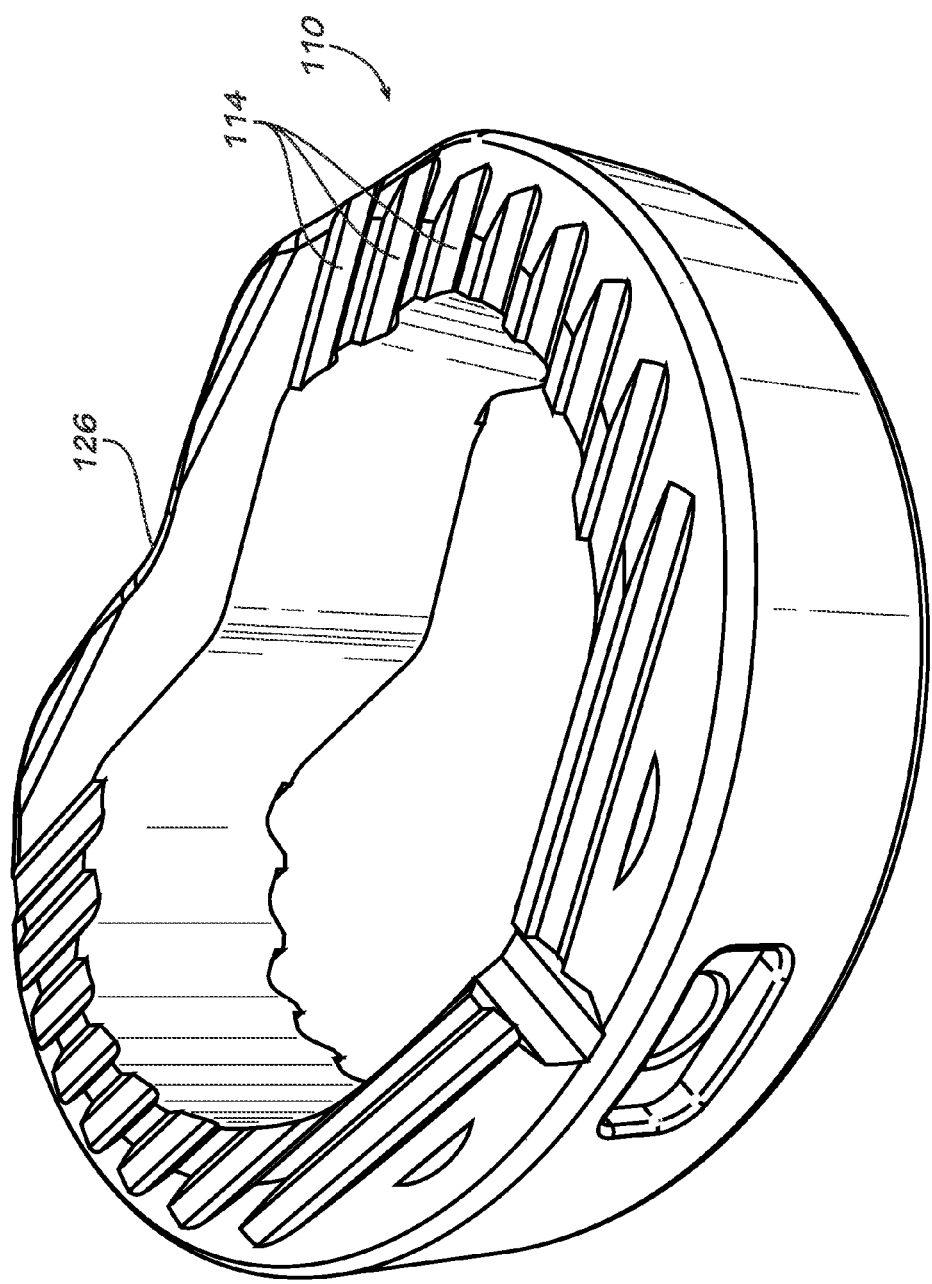
FIG. 7 is a perspective view of the implant of FIG. 5.

In certain other embodiments, as shown in FIGS. 5-7, implant 100, which is also generally kidney-bean shaped, includes teeth 114 having edges 113. As shown in FIG. 5, teeth 114 are arranged Chevron-style along both the superior and inferior surface of the implant, although the teeth 114 may be arranged along only one of such surfaces in other embodiments. Specifically, as shown in FIG. 6, a first tooth 115 on the lateral side of the implant has a longitudinal axis R that converges with the longitudinal axis Q of a second tooth 116 located on the medial side of the implant at the medial-lateral midline (M-L Midline). This orientation of the teeth has a "V" plow effect in that the teeth help the implant plow into the disc space along the desired path and help restrict migration in another direction. This allows for easier insertion into the disc space. Although the teeth shown in FIG. 6 are illustrated in a generally V-shaped pattern, the teeth could also be arranged in a double Chevron arrangement or so that the longitudinal axis of the teeth form a "U" or a "W" shape or any other suitable shape to achieve the desired plow effect.

The angulation of tooth edges 113 relative to the sagittal midline S (FIG. 5) of the implant restricts migration along both the medial-lateral (M-L) axis and the anterior-posterior (A-P) axis in the vertebral endplate plane. The tooth pattern may also include teeth having variable heights from anterior to posterior of the implant, such height being adjustable from posterior to anterior. The configuration of the Chevron teeth 114 of the implant 110 helps keep the implant from rotating.

Other embodiments may include a combination of the Chevron teeth (such as teeth 114) and radial teeth (such as teeth 14) arrangements to provide additional resistance to migration along multiple axes. Additionally, the toothed patterns may comprise angled teeth, castled teeth, parallel teeth, or other rigid surface designs to prevent movement and migration of the implant in multiple directions.

Figure 8:
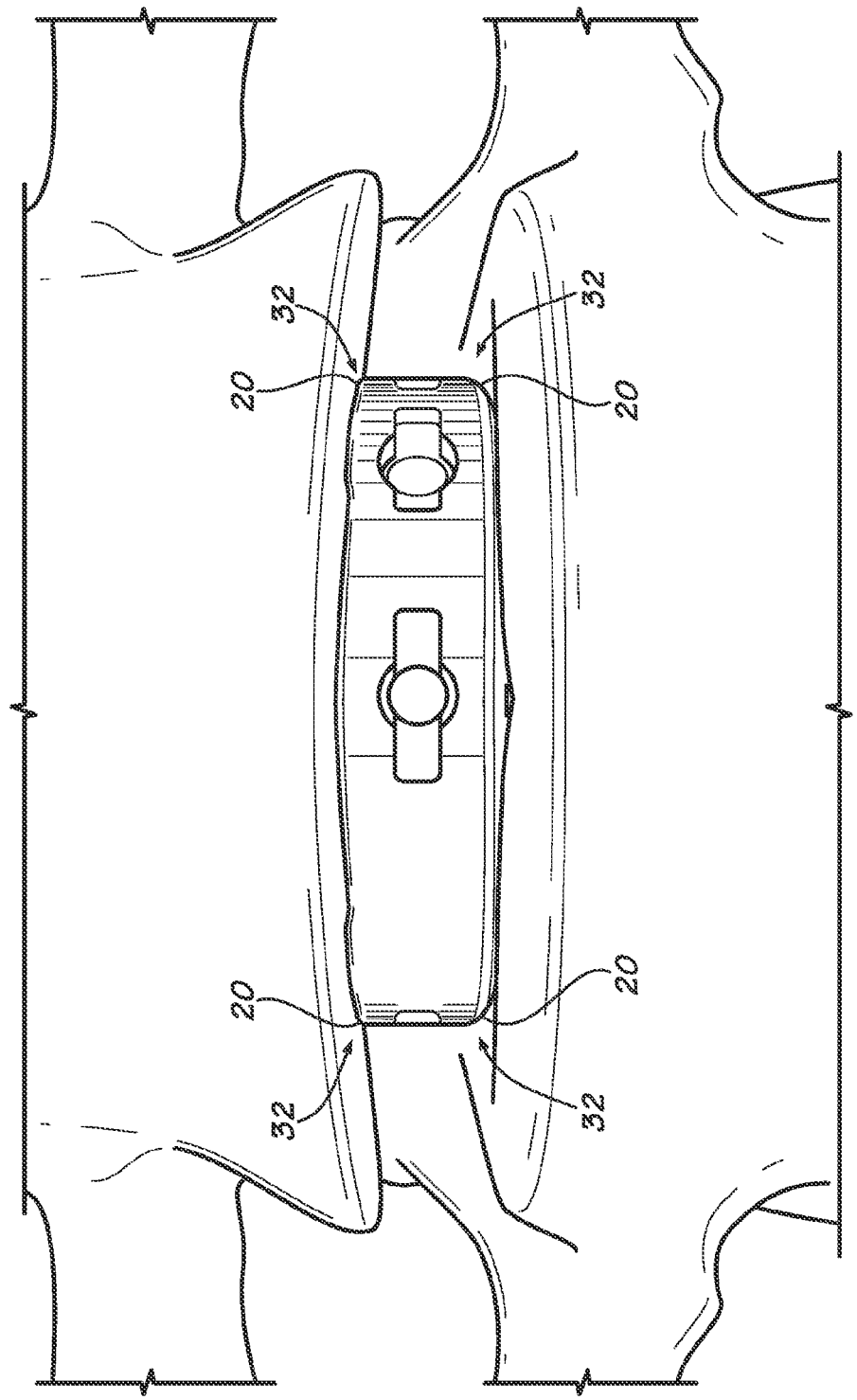
FIG. 8 is a front view of an implant according to one embodiment showing the anatomical contour matching of the implant.
Figure 9:
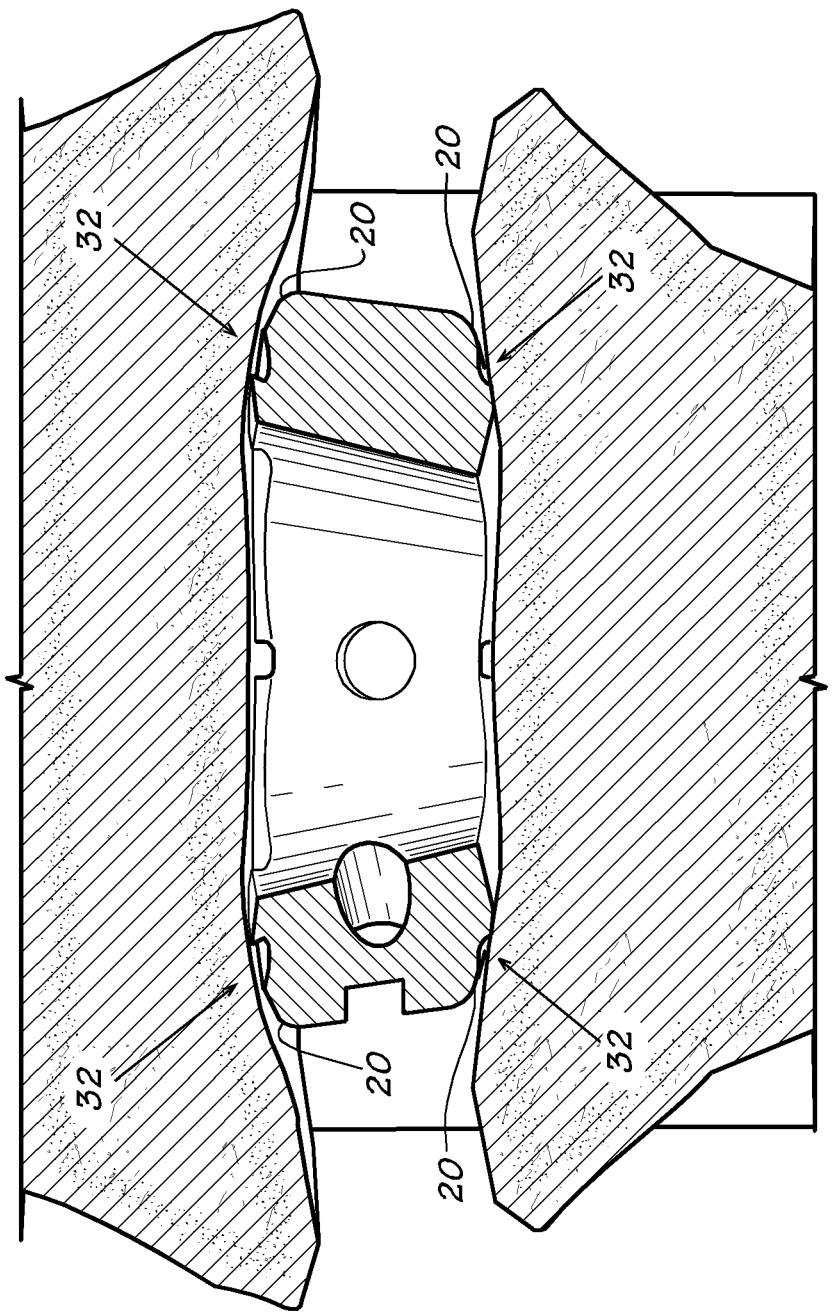
FIG. 9 is a cross-sectional view of the implant of FIG. 8.

In certain other embodiments of the invention, as shown in FIGS. 8-9, the implant comprises a peripheral contour 20 that is geometrically designed to match the contour of the surface of the vertebral disc space. The anatomical contour matching shown in FIGS. 8-9 allows for optimal surface contact with the vertebral endplate and thereby greater tooth engagement and reduced tendency for post operative migration of the implant. Specifically, as shown in FIGS. 8-9, the anatomical curvature of the vertebral endplate is matched by the peripheral contour 20 of the implant. In this way, the implant according to certain embodiments has an anatomical shape that provides a better fit for the interbody disc space. As shown in FIGS. 8-9, the curvature helps eliminate any pressure point contacts between the implant and the vertebral endplate that would otherwise exist at point contacts 32 if curvature 20 was replaced with sharp corners, such pressure point contacts tending to cause subsidence. Eliminating such pressure point contacts decreases the likelihood for pain and discomfort for the patient, and also provides more contact with the vertebral walls, reducing the likelihood of migration and movement and subsidence of the implant.

Figure 10:
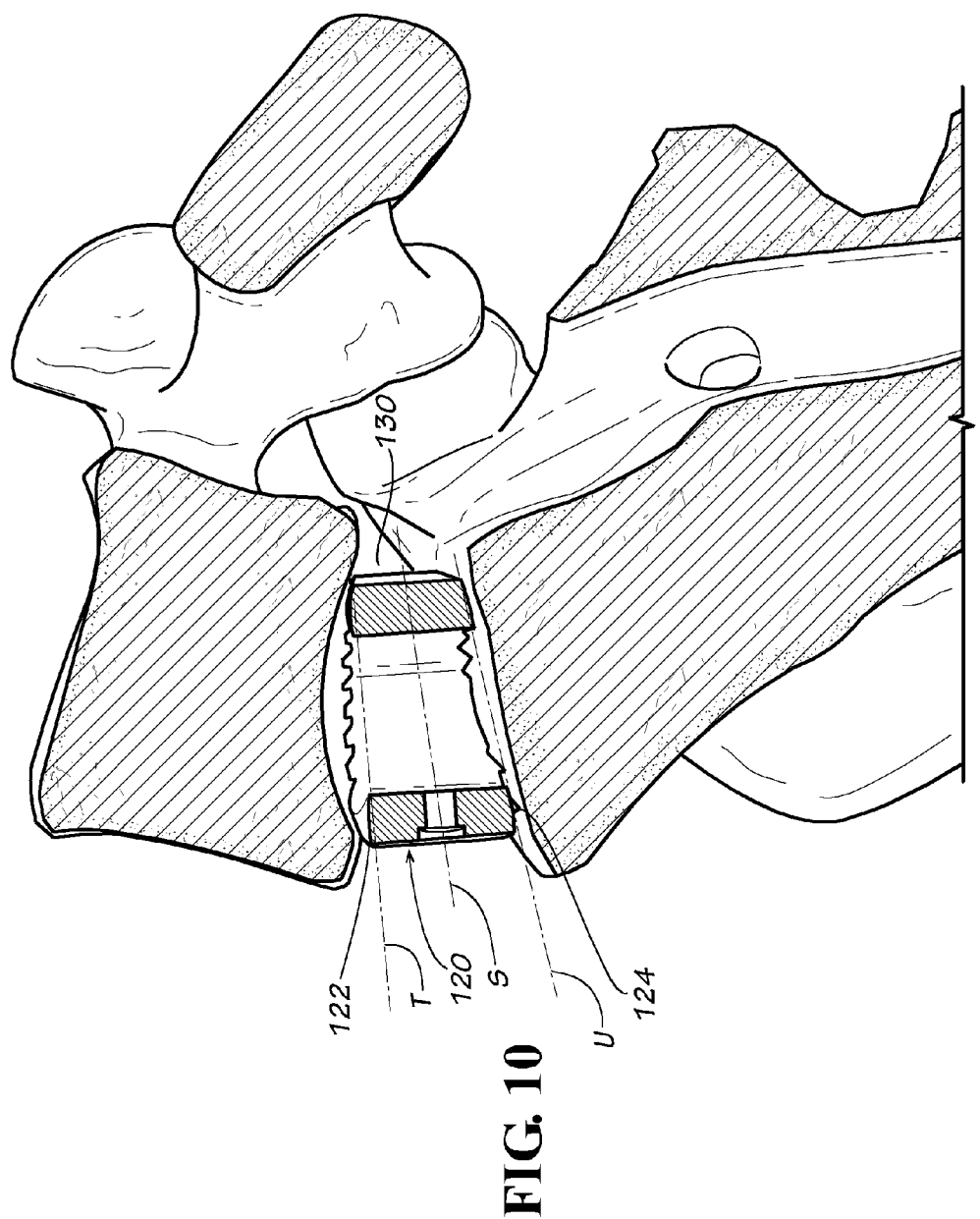
FIG. 10 shows an implant with midline asymmetry of surface angulation according to one embodiment.
Figure 11:
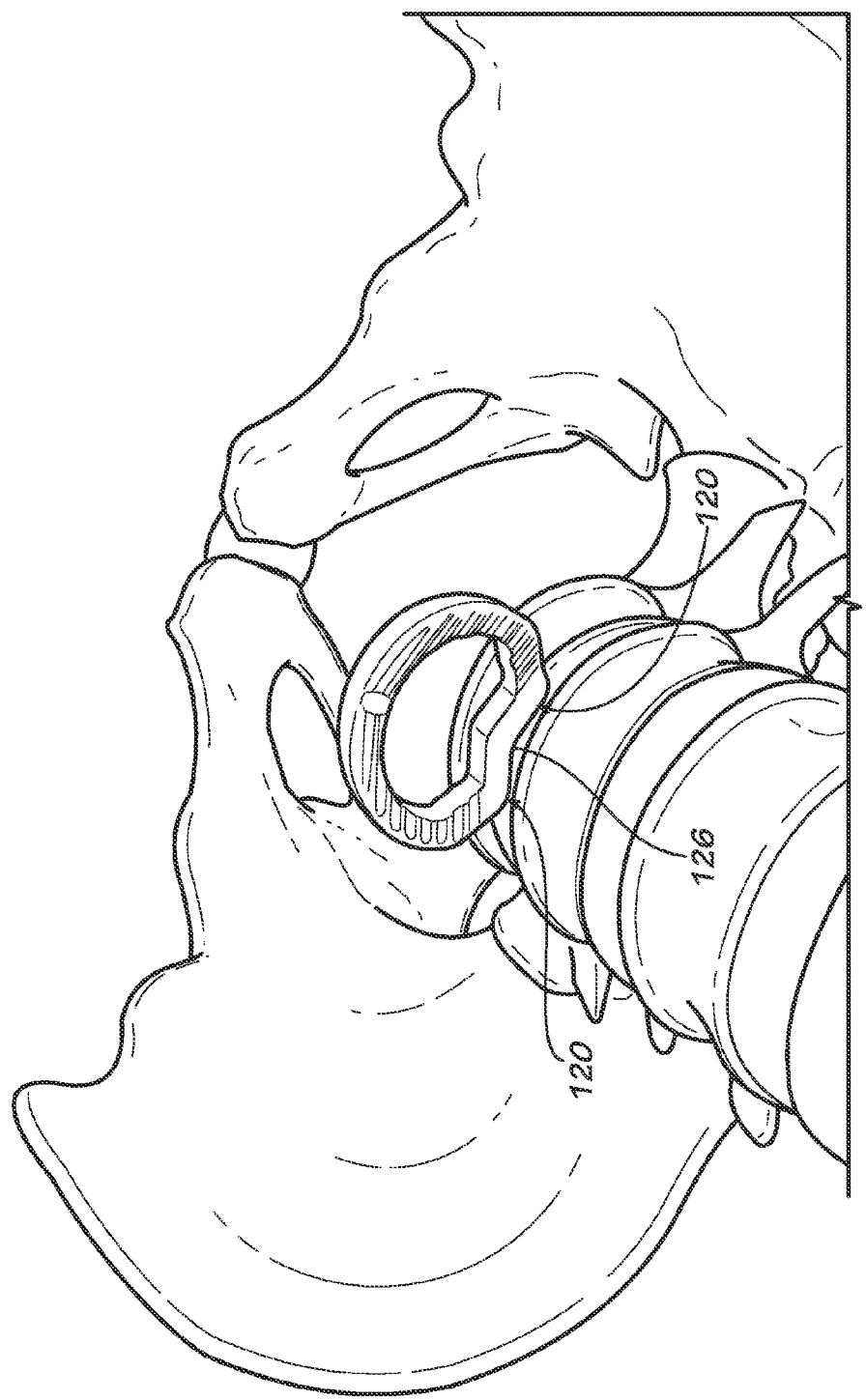
FIG. 11 shows an implant according to one embodiment prior to implantation.

Moreover, in some embodiments, as shown in FIG. 10, the implant 100 is asymmetric to better match the disc space (for example, above the sacrum and below the 5th lumbar vertebra (L5-S1), which is particularly asymmetric). The matching asymmetry of the implant surfaces results in optimal contact between the implant and the vertebral endplate and thus less post-operative migration of the implant. In certain embodiments, the implants may include independent variability in the lordotic angulation (curvature) of the superior and inferior implant surfaces. For example, the superior surface 122 may be convex or angled while the inferior surface 124 may have the same, opposite, or dissimilar angulation. In some embodiments, the angulation of the superior surface of the implant 100 relative to the midline S of the implant is different from the angulation of the inferior surface of the implant 100 to provide a better fit for the interbody space 130. Such variations in the lordotic angulation of the superior surface 122 and the inferior surface 124 relative to the midline S of the implant more closely matches the commonly asymmetric contours of the interbody disc space.

The implant 100 shown in FIG. 10 has a superior surface 122 that is generally parallel to the sagittal midline S, while the inferior surface 124 is sloped relative to the sagittal midline S. In some embodiments, the slope of line T associated with superior surface 122 relative to the sagittal midline S may range from about 0 degrees to about 20 degrees and the slope of line U associated with the inferior surface 124 relative to the sagittal midline S may range from about 0 to about 20 degrees. In one non-limiting example, the angulation of the superior surface (slope of line T) is about 0 degrees, while the angulation of the inferior surface (slope of the line U) is about 11 degrees. In another non-limiting example, the angulation of the superior surface (slope of line T) is about 3 degrees, while the angulation of the inferior surface (slope of the line U) is about 8 degrees. In certain non-limiting embodiments, the greater slope of the inferior half of the implant results in better matching of the implant to the geometry of the anatomical space, however this is not always the case. Additionally or alternatively, the curvature of the inferior and superior surfaces may be asymmetric in either or both the medial-lateral plane or the anterior-posterior plane.

Figure 12:
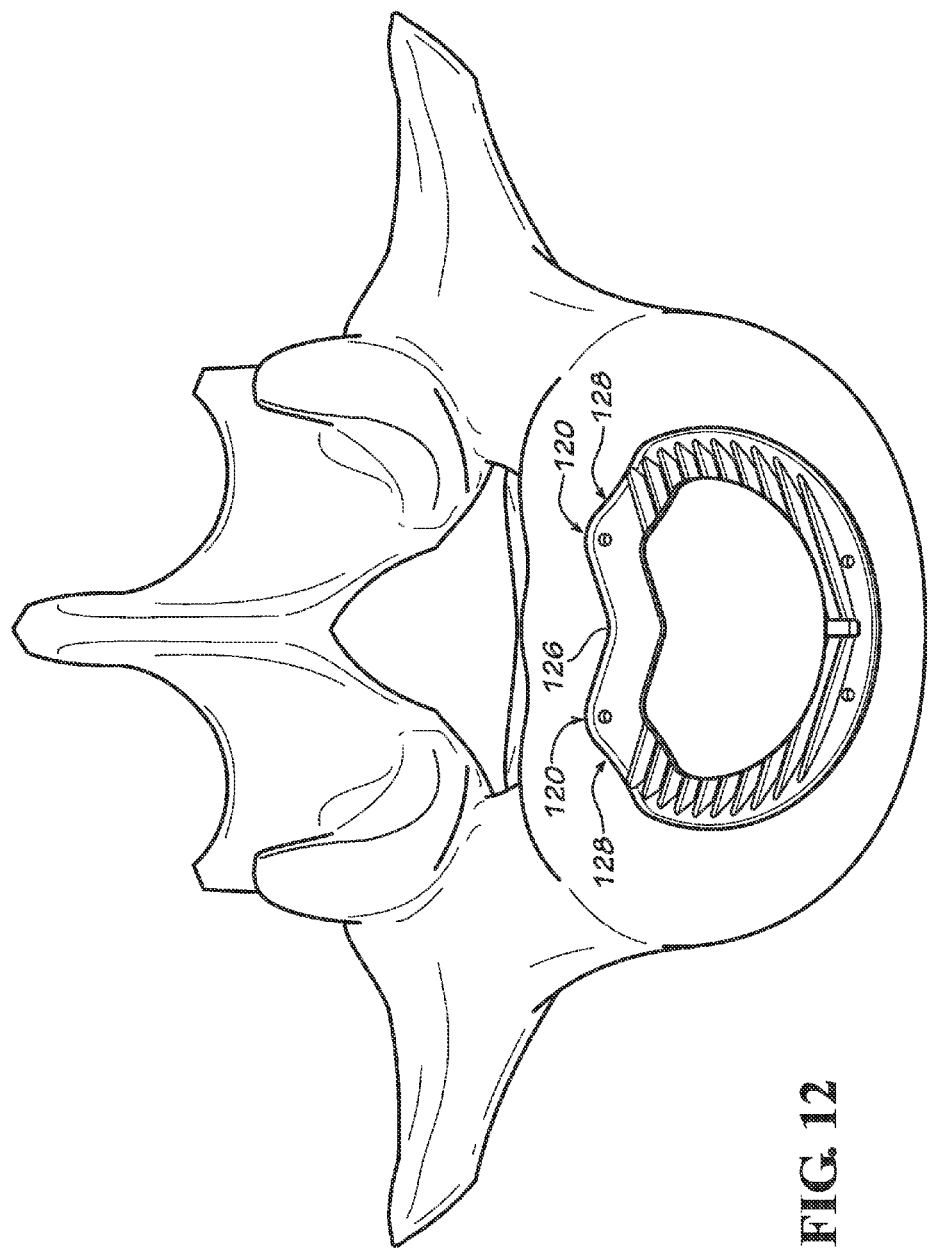
FIG. 12 is a top view of the implant of FIG. 11 after implantation.

The interbody implant used in certain embodiments may be designed to ease the distraction and insertion processes of spinal surgery. For example, in certain embodiments, the interbody implant may have a bulleted nose, a rounded nose, rounded surface, or other similar design to aid in the distraction of the disc space during insertion of the implant. As shown in FIGS. 3 and 6, the posterior portion of the implant may have a leading edge 18, 118, that forms a notch 26, 126 that results in a two point contact of the implant edge with the disc space opening, thereby enhancing the initial stability of the implant/inserter assembly. The two points of contact 120 as the implant is positioned to be introduced into the disc space are illustrated in FIG. 10. The two points of contact 120 help maintain the location of the implant as it is implanted because the two points of contact 120 rest against the spine and provide a stable resting position for the implant during impaction. Moreover, as shown in FIG. 12, notch 126 reduces the likelihood of tissue compression against the spinal cord after insertion in the disc space. The implant may also include notches 128 (FIG. 12) that help reduce the likelihood of tissue compression against the nerve roots. In some embodiments, notch 126 is generally V-shaped, although notch 126 could have any suitable shape. Alternatively or additionally, the leading edge of the implant may include chamfered or rounded corners to mimic the disc space anatomy and to avoid the neural or vascular structures during insertion into the disc space. The interbody implant according to certain embodiments may additionally or alternatively include a radius to the top, bottom, and/or both sides to mimic the disc space. The implant may additionally or alternatively contain a rounded surface on the anterior side of the implant to fit into the disc space and allow the denser, cortical edges of the vertebral bodies to rest more anatomically and prevent migration through the endplates of the bodies. Also, the implant may be wider in the anterior-posterior dimension as well as medial-lateral dimension to prevent the pistoning through the endplate. For example, the implant according to certain embodiments may include at least one arcuate, slightly expanded side wall 34 (FIG. 3) to mimic the disc space for a more anatomical fit.

In certain other embodiments, the implant may include additional features that aid in the insertion of the implant into the interbody disc space and, once inserted, prevents movement, migration, and/or repulsion of the implant. The implant may also include attached screws for fixating the implant to the vertebral bone. Alternatively, the implant may include holes for receiving bone screws. The interbody implant of the present invention may be attachable to a fixation plate. The implant may additionally or alternatively include a locking mechanism to prevent the implant from disengaging from the fixation plate.

In certain embodiments, the implant may be engaged by an insertion tool to further aid in delivering the implant to the interbody disc space. The implant may include multiple insertion points for an inserter tool.

The implant according to certain embodiments may also include fenestrations on at least one side to allow bone to grow through the interbody implant. The fenestrations may be of different sizes and geometries designed to retain bone graft material during insertion of the interbody implant into the disc space. For example, in certain embodiments, the fenestrations may include a mesh system to hold in the graft material to keep it from falling out during insertion of the interbody implant. In alternative embodiments, other methods, materials, and geometrical fenestrations are used in connection with the implant to retain the graft material in the interbody implant.

The foregoing is provided for purposes of illustrating, explaining, and describing embodiments of the present invention. Further modifications and adaptations to these embodiments will be apparent to those skilled in the art and may be made without departing from the scope or spirit of the invention.

The invention claimed is:
1. A spinal implant device comprising:
 a body for holding graft material therein, the body comprising:
  a sagittal midline;
  a posterior edge and an anterior edge opposite the posterior edge;

a superior surface and an inferior surface opposite the superior surface, at least one of the superior surface and the inferior surface comprising a plurality of teeth;

wherein the plurality of teeth comprises a first row of outer teeth positioned circumferentially along a peripheral edge of the body and a second row of inner teeth positioned inwardly from the first row of outer teeth;

wherein the first row of outer teeth each comprise an outer side and an inner side that meets with the outer side to form an outer tooth edge at a peak of each respective outer tooth, the outer tooth edge of each respective outer tooth configured to contact a vertebral endplate;

wherein the first row of outer teeth is positioned circumferentially along the peripheral edge of the body such that the vertebral endplate contacting outer tooth edge of each outer tooth of the first row of outer teeth is not parallel to vertebral endplate contacting outer tooth edges of adjacent teeth of the first row of outer teeth; and wherein the vertebral endplate contacting outer tooth edges of the first row of outer teeth are configured to contact the vertebral endplate to resist migration of the implant in two directions; and wherein the inner teeth of the second row project further from the sagittal midline than an outwardly adjacent outer tooth of the first row of outer teeth.

2. The spinal implant device of claim 1, wherein the second row of inner teeth each comprise an outer side and an inner side that meets with the outer side to form an inner tooth edge at a peak of each respective inner tooth, the inner tooth edge of each respective inner tooth configured to contact the vertebral endplate;

wherein the second row of inner teeth is positioned radially such that the vertebral endplate contacting inner tooth edge of each tooth of the second row of inner teeth is not parallel to vertebral endplate contacting inner tooth edges of adjacent teeth of the second row of inner teeth;

wherein the inner tooth edges of the second row of inner teeth are configured to resist migration of the implant in two directions; and wherein the outer tooth edges of the first row of outer teeth and the inner tooth edges of the second row of inner teeth together are configured to resist movement and migration of the spinal implant in a medial-lateral axis and an anterior-posterior axis;

wherein a slope of the outer side of each outer tooth from the respective tooth edge toward the sagittal midline is less than a slope of the inner side of each respective outer tooth from the respective tooth edge toward the sagittal midline; and wherein a slope of the outer side of each inner tooth from the respective tooth edge toward the sagittal midline is greater than a slope of the inner side of each respective inner tooth from the respective tooth edge toward the sagittal midline.

3. The spinal implant device of claim 2, further comprising a trough disposed between the first row of outer teeth and the second row of inner teeth, and wherein the slope of the outer side of each respective outer tooth from the respective outer tooth edge toward the sagittal midline is greater than the slope of the inner side of each respective inner tooth from the respective inner tooth edge toward the sagittal midline.

4. The spinal implant device of claim 2, wherein the first row of outer teeth slopes to the anterior edge of the body so that the outer side of each outer tooth faces outwardly from the implant toward the anterior edge and forms a perimeter edge of the implant that is configured to limit point contacts between the perimeter edge of the implant and a vertebral endplate.

5. The spinal implant device of claim 1, wherein each tooth of the plurality of teeth are configured to avoid point contact with vertebral endplates.

6. The spinal implant device of claim 2, wherein the body defines a central opening and wherein the inner side of each tooth of the second row of inner teeth slopes toward and to the central opening.

7. A spinal implant device comprising:
a body for holding graft material therein, the body comprising:
a sagittal midline;
a posterior edge and an anterior edge opposite the posterior edge;
a superior surface and an inferior surface opposite the superior surface, at least one of the superior surface and the inferior surface comprising a plurality of teeth;
wherein the plurality of teeth comprises a first row of outer teeth positioned along a peripheral edge of the body and a second row of inner teeth positioned inwardly from the first row of outer teeth; and
wherein a trough separates each tooth of the first row of outer teeth from each tooth of the second row of inner teeth that is inwardly adjacent from each tooth of the first row of outer teeth;
wherein each of the outer teeth of the first row of outer teeth comprises an outer side and an inner side that meets with the outer side to form an outer tooth edge at a peak of each respective outer tooth, the outer tooth edge of each respective outer tooth configured to contact a vertebral endplate while avoiding point contact with the vertebral endplate, and wherein a slope of the outer side of each outer tooth from the respective outer tooth edge toward the sagittal midline is less than a slope of the inner side of each respective outer tooth from the respective outer tooth edge toward the sagittal midline;
wherein each of the inner teeth of the second row of inner teeth comprises an outer side and an inner side that meets with the outer side to form an inner tooth edge at a peak of each respective inner tooth, the inner tooth edge of each respective inner tooth configured to contact the vertebral endplate while avoiding point contact with the vertebral endplate, and wherein a slope of the outer side of each inner tooth from the respective inner tooth edge toward the sagittal midline is greater than a slope of the inner side of each respective inner tooth from the respective inner tooth edge toward the sagittal midline.

8. The spinal implant device of claim 7, wherein the first row of outer teeth slopes to the anterior edge of the body so that the outer side of each outer tooth faces outwardly from the implant toward the anterior edge and forms a perimeter edge of the implant that is configured to limit point contacts between the perimeter edge of the implant and a vertebral endplate.

9. The spinal implant device of claim 7, wherein the body defines a central opening and wherein the inner side of each of the second row of inner teeth slopes toward and to the central opening.

10. A spinal implant device comprising:
a body for holding graft material therein, the body having comprising:

a sagittal midline;
a posterior edge and an anterior edge opposite the posterior edge;
a superior surface and an inferior surface opposite the superior surface, at least one of the superior surface and the inferior surface comprising a plurality of teeth;
wherein the plurality of teeth comprises a first row of outer teeth positioned along a peripheral edge of the body and a second row of inner teeth positioned inwardly from the first row of outer teeth; and
wherein the outer teeth each comprise an outer side and an inner side that meets with the outer side to form an outer tooth edge at a peak of each respective outer tooth, the outer tooth edge of each respective outer tooth configured to contact a vertebral endplate, and wherein a slope of the outer side of each outer tooth from the respective outer tooth edge toward the sagittal midline is less than a slope of the inner side of each respective outer tooth from the respective outer tooth edge toward the sagittal midline;
wherein the first row of outer teeth is positioned circumferentially along the peripheral edge of the body such that the vertebral endplate contacting outer tooth edge of each tooth of the first row of outer teeth is not parallel to vertebral endplate contacting outer tooth edges of adjacent teeth of the first row of outer teeth, the vertebral endplate contacting outer tooth edges of the first row of outer teeth being configured to resist migration of the implant in two directions;
wherein the inner teeth each comprise an outer side and an inner side that meets with the outer side to form an inner tooth edge at a peak of each respective inner tooth, the inner tooth edge of each respective inner tooth configured to contact the vertebral endplate, and wherein a slope of the outer side of each inner tooth from the respective inner tooth edge toward the sagittal midline is greater than a slope of the inner side of each respective inner tooth from the respective inner tooth edge toward the sagittal midline;
wherein the second row of inner teeth is positioned radially such that the vertebral endplate contacting inner tooth edge of each tooth of the second row of inner teeth is not parallel to vertebral endplate contacting inner tooth edges of adjacent teeth of the second row of inner teeth;
wherein the vertebral endplate contacting outer tooth edges of the first row of outer teeth and the vertebral endplate contacting inner tooth edges of the second row of inner teeth together are configured to resist movement and migration of the spinal implant in a medial-lateral axis and an anterior-posterior axis.

11. The spinal implant device of claim 10, wherein the slope of the outer side of each respective outer tooth from the respective outer tooth edge toward the sagittal midline is greater than the slope of the inner side of each respective inner tooth from the respective inner tooth edge toward the sagittal midline.

12. The spinal implant device of claim 10, wherein the first row of outer teeth slopes to the anterior edge of the body so that the outer side of each outer tooth faces outwardly from the implant toward the anterior edge and forms a perimeter edge of the implant that is configured to limit point contacts between the perimeter edge of the implant and a vertebral endplate.

13. A spinal implant device comprising:
a body for holding graft material therein, the body comprising:
a sagittal midline;
a superior surface and an inferior surface opposite the superior surface, at least one of the superior surface and the inferior surface comprising a plurality of teeth;
a posterior edge and an anterior edge opposite the posterior edge, the posterior edge of the body including a first notch and second and third notches adjacent to the first notch on opposite sides of the first notch, the second and third notches configured to limit tissue compression against nerve roots in a vertebral disc space;
wherein the plurality of teeth comprises a first row of outer teeth positioned circumferentially along a peripheral edge of the body and a second row of inner teeth positioned inwardly from the first row of outer teeth;
wherein each of the outer teeth of the first row of outer teeth comprises an outer side and an inner side that meets with the outer side to form an outer tooth edge at a peak of each respective outer tooth, the outer tooth edge of each respective outer tooth configured to contact a vertebral endplate, and wherein a slope of the outer side from the respective outer tooth edge toward the sagittal midline is less than a slope of the inner side of each respective outer tooth from the respective outer tooth edge toward the sagittal midline;
wherein each of the inner teeth of the second row of inner teeth comprises an outer side and an inner side that meets with the outer side to form an inner tooth edge at a peak of each respective inner tooth, the inner tooth edge of each respective inner tooth configured to contact the vertebral endplate, and wherein a slope of the outer side from the respective inner tooth edge toward the sagittal midline is greater than a slope of the inner side of each respective inner tooth from the respective inner tooth edge toward the sagittal midline;
wherein the first row of outer teeth is positioned circumferentially along the peripheral edge of the body such that the vertebral endplate contacting outer tooth edge of each outer tooth of the first row of outer teeth is not parallel to vertebral endplate contacting outer tooth edges of adjacent teeth of the first row of outer teeth; and
wherein a trough separates each tooth of the first row of outer teeth from each tooth of the second row of inner teeth that is inwardly adjacent from each tooth of the first row of outer teeth, and
wherein each tooth of the plurality of teeth is configured to avoid point contact with vertebral endplates; and
wherein the vertebral endplate contacting outer tooth edges of the first row of outer teeth and the vertebral endplate contacting inner tooth edges of the second row of inner teeth are configured to contact the vertebral endplate and together are configured to resist movement and migration of the spinal implant in a medial-lateral axis and an anterior-posterior axis; and
wherein the inner teeth of the second row project further from the sagittal midline than an outwardly adjacent outer tooth of the first row of outer teeth.

14. The spinal implant device of claim 13, wherein the slope of the outer side of each respective outer tooth from the respective outer tooth edge toward the sagittal midline is greater than the slope of the inner side of each respective inner tooth from the respective inner tooth edge toward the sagittal midline.

15. The spinal implant device of claim 13, wherein the first row of outer teeth slopes to the anterior edge of the body so that the outer side of each outer tooth faces outwardly from the implant toward the anterior edge and forms a perimeter edge of the implant that is configured to limit point contacts between the perimeter edge of the implant and a vertebral endplate.

* * * * *